US008494111B2

(12) United States Patent
Nakanishi et al.

(10) Patent No.: US 8,494,111 B2
(45) Date of Patent: Jul. 23, 2013

(54) SYSTEM AND METHOD FOR IMAGE RECONSTRUCTION FOR HELICAL CONE BEAM COMPUTED TOMOGRAPHY WITH FACTORIZED REDUNDANCY WEIGHTING

(75) Inventors: Satoru Nakanishi, Tochigi-ken (JP);
Aleksandr Zamyatin, Buffalo Grove, IL (US)

(73) Assignees: Kabushiki Kaisha Toshiba, Tokyo (JP);
Toshiba Medical Systems Corporation, Otawara-shi (JP)

( * ) Notice: Subject to any disclaimer, the term of this patent is extended or adjusted under 35 U.S.C. 154(b) by 186 days.

(21) Appl. No.: 12/244,590

(22) Filed: Oct. 2, 2008

(65) Prior Publication Data

US 2009/0154639 A1    Jun. 18, 2009

Related U.S. Application Data

(60) Provisional application No. 60/985,161, filed on Nov. 2, 2007.

(51) Int. Cl.
*A61B 6/03* (2006.01)

(52) U.S. Cl.
USPC .................................. 378/15; 378/4; 382/131

(58) Field of Classification Search
USPC ................................ 378/4, 15; 382/128–132
See application file for complete search history.

(56) References Cited

U.S. PATENT DOCUMENTS

2004/0252806 A1 * 12/2004 Taguchi et al. ................... 378/4
2006/0067457 A1 * 3/2006 Zamyatin et al. ................. 378/4

FOREIGN PATENT DOCUMENTS

JP    2006-95297    4/2006

OTHER PUBLICATIONS

Zamyatin et al., Helical CT Reconstruction with Large Cone Angle, published May 7, 2007, IEEE Nuclear Science Symposium Record 2006, pp. 2264-2267.*
Zamyatin et al., Reconstruction Algorithm for Wide Cone Beam Helical CT, Feb. 27, 2006, 2005 IEEE Nuclear Science Symposium Conference Record, pp. 2278-2282.*
Smith, IEEE San Diego 2006 Conference Program, Oct. 2006, pp. 1-7 and 112-113.*
Taguchi et al., A new weighting scheme for cone-beam helical CT to reduce the image noise, 2004, Physics in Medicine and Biology, vol. 49, pp. 2351-2364.*
Japanese Office Action mailed on Jan. 22, 2013 in corresponding Application No. 2008-283542 (with English Translation).

* cited by examiner

*Primary Examiner* — Toan Ton
*Assistant Examiner* — John Corbett
(74) *Attorney, Agent, or Firm* — Oblon, Spivak, McClelland, Maier & Neustadt, L.L.P.

(57) ABSTRACT

A method and system for computed tomography were weighted data is used to reconstruct an image. The apparatus includes an x-ray source producing a cone-beam of x-rays, an x-ray detector disposed to receive x-rays from the x-ray source, a data collection unit, and a processing unit for processing the data using a weighting function using contributions from fan-beam and cone-beam weighting functions. The apparatus can produce images with reduced artifacts.

15 Claims, 5 Drawing Sheets

Conventional filtering along detector rows

Tangential filtering directions

Katsevich filtering directions

SYSTEM AND METHOD FOR IMAGE RECONSTRUCTION FOR HELICAL CONE BEAM COMPUTED TOMOGRAPHY WITH FACTORIZED REDUNDANCY WEIGHTING

BACKGROUND OF THE INVENTION

1. Field of the Invention

The present invention relates to computed tomographic (CT) imaging, and in particular to weighting in helical cone-beam CT.

2. Discussion of the Background

As medical CT manufacturers produce scanners with increasing number of detector rows, there arises a need for a practical reconstruction algorithm that can handle the increasing cone angle. Recently an exact helical cone beam algorithm of the shift invariant FBP type (Katsevich algorithm) was proposed, suitable for 1-PI and 3-PI reconstruction. After that practical ways to implement Katsevich algorithm in medical CT scanners were investigated. Generally, exact helical algorithms use only data within the helical PI-intervals, or, equivalently, within the N-PI window [10-11], where N=1, 3, . . . , is the number of helical half-turns used in reconstruction. However from the practical point of view N-PI window weighting has the following properties:

1) Some measured data located outside the N-PI window is not used, which means extra dose to the patient.

2) All data within the N-PI window is used with the same weight; while it is beneficial to the noise reduction, it makes an algorithm more sensitive to patient motion and imperfections of real data.

3) The N-PI reconstruction restricts the choice of the helical pitch. For example, pitches in the range of 0.75-0.85 are too fast to be used with the 3-PI window, and are suboptimal to use with the 1-PI window, since only a small fraction of data is utilized.

On the other hand, 2D fan beam redundancy weighting has the following advantages:

1) Easily adjusted to the helical pitch

2) Smooth transition from 0 to 1 makes an algorithm more stable to patient motion and imperfections of real data.

SUMMARY OF THE INVENTION

The present invention is directed to a CT method and apparatus where, in one embodiment, the apparatus includes an x-ray source, an x-ray detector disposed to receive x-rays from the x-ray source, a data collection unit, a processing unit for processing the data using a weighting function given as $$w_{CB}(\beta, \gamma, v) = \frac{u_{FB}(\beta) \cdot u_{CB}(v, \gamma)}{\sum_{n=-N}^{N} (u_{FB}(\beta_n(\beta, \gamma)) \cdot u_{CB}(v_n))}$$

where $\beta$ is a projection angle of said x-rays, $\gamma$ is a fan angle of said x-rays, and $v$ is a detector coordinate parallel to axis of rotation of said x-ray source.

In another embodiment, the method includes exposing a subject to x-rays from an x-ray source, collecting data, weighting the data using $$w_{CB}(\beta, \gamma, v) = \frac{u_{FB}(\beta) \cdot u_{CB}(v, \gamma)}{\sum_{n=-N}^{N} (u_{FB}(\beta_n(\beta, \gamma)) \cdot u_{CB}(v_n))}$$

and reconstructing an image of the subject using the weighted data

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION

Figure 1:
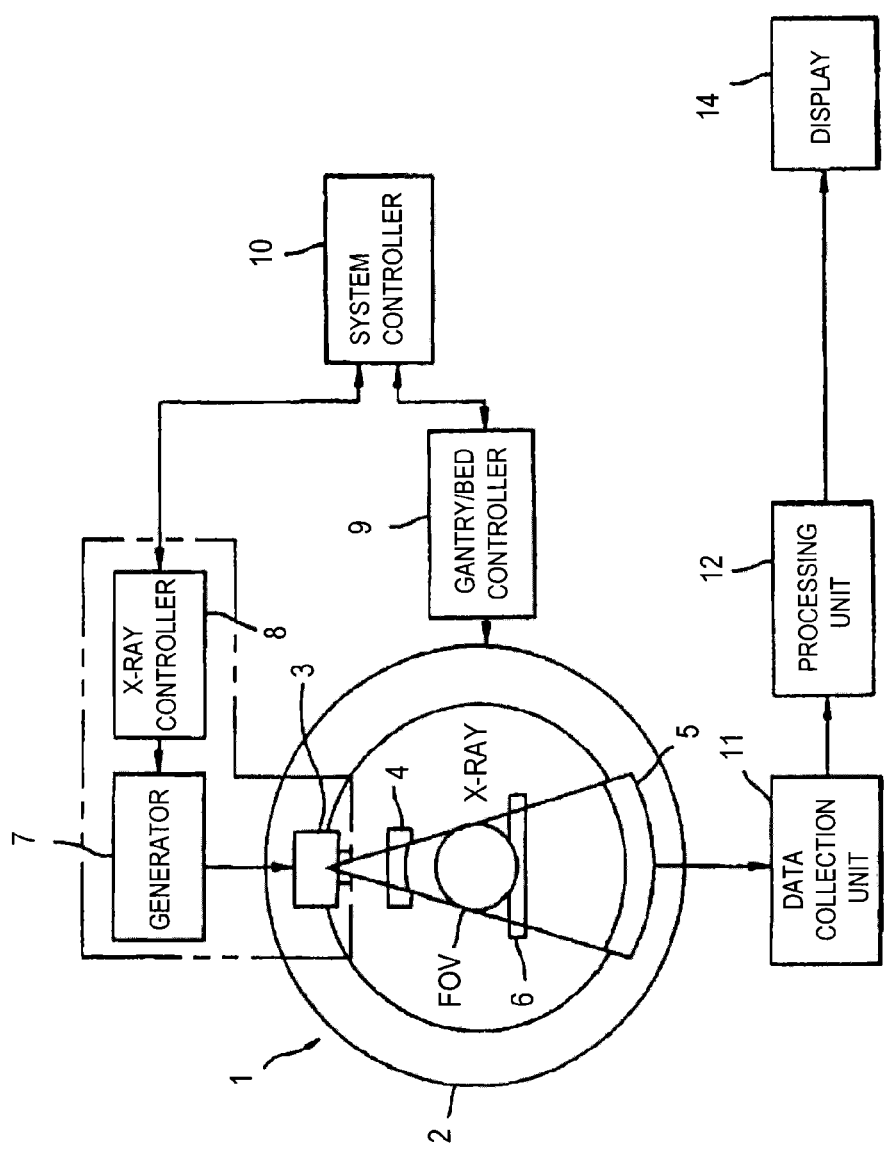
FIG. 1 is a diagram of a system according to the invention.

FIG. 1 shows an x-ray computed topographic imaging device according to the present invention. The projection data measurement system constituted by gantry 1 accommodates an x-ray source 3 that generates a cone-beam of x-ray flux approximately cone-shaped, and a two-dimensional array type x-ray detector 5 consisting of a plurality of detector elements arranged in two-dimensional fashion, i.e., a plurality of elements arranged in one dimension stacked in a plurality of rows. X-ray source 3 and two-dimensional array type x-ray detector 5 are installed on a rotating ring 2 in facing opposite sides of a subject, who is laid on a sliding sheet of a bed 6. Two-dimensional array type x-ray detector 5 is mounted on rotating ring 2. Each detector element will correspond with one channel. X-rays from x-ray source 3 are directed on to subject through an x-ray filter 4. X-rays that have passed through the subject are detected as an electrical signal by two-dimensional array type x-ray detector 5.

X-ray controller 8 supplies a trigger signal to high voltage generator 7. High voltage generator 7 applies high voltage to x-ray source 3 with the timing with which the trigger signal is received. This causes x-rays to be emitted from x-ray source 3. Gantry/bed controller 9 synchronously controls the revolution of rotating ring 2 of gantry 1 and the sliding of the sliding sheet of bed 6. System controller 10 constitutes the control center of the entire system and controls x-ray controller 8 and gantry/bed controller 9 and x-rays are emitted continuously or intermittently at fixed angular intervals from x-ray source 3.

The output signal of two-dimensional array type x-ray detector 5 is amplified by a data collection unit 11 for each channel and converted to a digital signal, to produce projection data. The projection data that is output from data collection unit 11 is fed to processing unit 12. Processing unit 12 performs various processing using the projection data. Unit 12 performs data sampling and shifting (described in more detail below), filtering, backprojection and reconstruction, as well as other desired operation on the projection data. Unit 12 determines backprojection data reflecting the x-ray absorption in each voxel. In the circular scanning system using a cone-beam of x-rays as in the first embodiment, the imaging region (effective field of view) is of cylindrical shape of radius R centered on the axis of revolution. Unit 12 defines a plurality of voxels (three-dimensional pixels) in this imaging region, and finds the backprojection data for each voxel. The three-dimensional image data or tomographic image data compiled by using this backprojection data is sent to display device 14, where it is displayed visually as a three-dimensional image or tomographic image.

Figure 2:
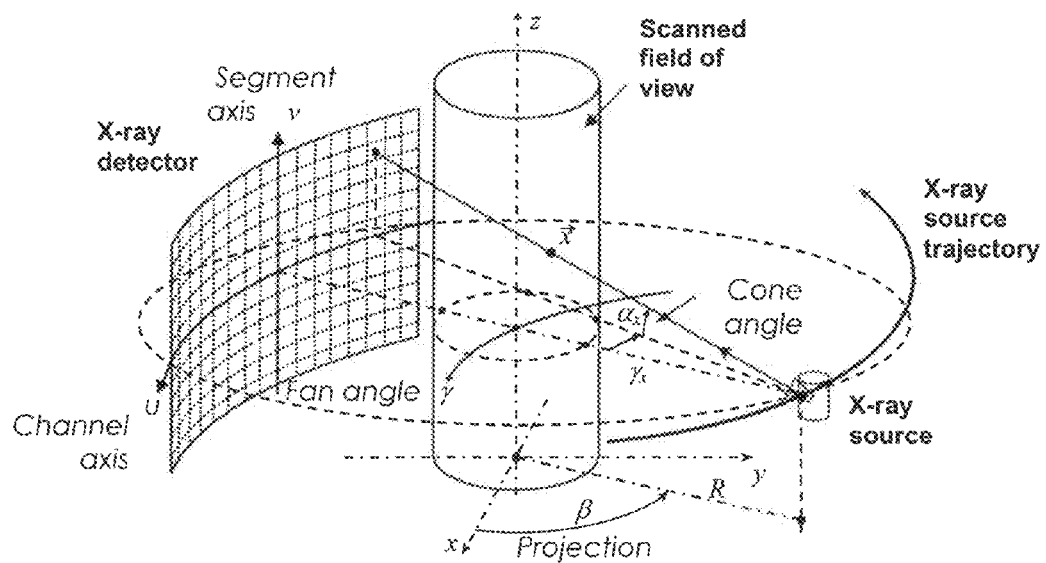
FIG. 2 is a diagram of scanning geometry.

The system geometry for explaining the apparatus and method according to the invention is shown in FIG. 2. The apparatus and system are directed to a cone-beam system. X-rays are emitted at a plurality of projection angles around the object to collect at least minimally required tomographic data. At each projection angle $\beta$, x-rays are emitted with a cone angle $\gamma$ and a fan angle $\alpha$ and pass through an object with a scanned field of view. The source follows a helical trajectory. The rays are detected by the two-dimensional detector.

A two-dimensional detector can be described where each detector element k, k=1 . . . Nseg×M, where Nseg is the number of detector rows, and M is the number of elements per detector row.

Intensity of the x-ray photon beam (ray) at the detector element k, attenuated by an object or patient, is given by:

$$I_k = I_k^0 \exp(-\int \mu(x) dx), \quad (1)$$

where $\mu(x)$ is the attenuation function to be reconstructed, $I_k^0$ is the beam intensity before attenuation by $\mu(x)$, as produced by the x-ray tube and after penetrating through the x-ray (wedge, bowtie) filter, and $\int \mu(x) dx$ is the line integral of $\mu(x)$ along the line l. Mathematically, $\mu(x)$ can be reconstructed given a set of line integrals corresponding to a plurality of lines l. Therefore, measured intensity data are to be converted into line integrals first $$\int \mu(x) dx = \ln(I_k^0) - \ln(I_k) \quad (2)$$

X-ray tomographic reconstruction consists of the following three main steps, data acquisition, data processing and data reconstruction. In data acquisition, the x-ray intensity data are collected at each detector element and each predefined angular view position. This is done within rotating part of the gantry 1. Detector 5 measures incident x-ray flux and converts it into an electric signal. There are two main types of detectors: energy (charge) integrating and photon counting. The electric signal is transferred from a rotating part of the gantry 1 to stationary part though the slipring 2. During this step data may be compressed.

In data processing, data is converted from x-ray intensity measurements to the signal corresponding to line integrals according to equation (2). Also, various corrections steps are applied to reduce effects of undesired physical phenomena, such as scatter, x-ray beam hardening, compensate non-uniform response function of each detector element, and to reduce noise.

Depending on the algorithm, data reconstruction contains all or some of the following processing steps:

Cosine (fan angle, cone angle) weighting (can be ×cos, or 1/cos)

Data differentiation. It can be performed with respect to fan angle, cone angle, projection angle, source trajectory coordinate, vertical detector coordinate, horizontal detector coordinate, or any combination of those.

Data redundancy weighting. Data is multiplied by the weight function W, which may be a function of fan angle, cone angle, projection angle, source trajectory coordinate, vertical detector coordinate, horizontal detector coordinate, or any combination of those.

Convolution (filtering). This step utilizes convolution kernel. Some algorithms use ramp-based kernel (H(w)=|w|), some use Hilbert-based kernel (h(t)=1/t, h(t)=1/sin(t), H(w)=i sign(w)). Kernels can be adjusted to the fan beam geometry, scaled, modulated, apodised, modified, or any combination of those. Filtering can be applied along non-horizontal directions, in which case data resampling to the filtering directions and possibly inverse resampling to the original detector grid is required.

Backprojection. In this step data is projected back in the image domain. Usually, backprojected data is weighted by a distance factor. Distance factor is inversely proportional to the distance L from the x-ray source position to the reconstructed pixel. Distance factor can be proportional to 1/L or $1/L^2$. Also, some additional data redundancy weighting can be applied here on the pixel-by-pixel basis. Also, usually backprojection step includes obtaining data value corresponding to the ray through the reconstructed pixel by either data interpolation or data extrapolation. This process can be done in a numerous variety of ways.

The order in which the above steps are applied depends on a specific reconstruction algorithm.

In the present invention, the processing unit performs data redundancy weighting, termed smooth cone beam weighting, in the following manner. Here, $\beta$ is the projection angle, $\gamma$ is the fan angle, $v$ is the detector coordinate parallel to the axis of rotation, $\alpha$ is the cone angle where $v = R \tan \alpha$, $g(\beta, \gamma, v)$ is the cone beam data along the helical source trajectory $\lambda(\beta) = (R \cos \beta, R \sin \beta, \beta H/2\pi)$, with radius R and pitch H. The physical size of the detector limits detector coordinates to $-v_{max} < v < v_{max}$, and $-\gamma_{max} < \gamma < \gamma_{max}$. In reconstructing an image plane P, normally horizontal planes are reconstructed, so P is given by the equation $z = z_0$. The values of $v$ are within the scan range $[\beta_{start}, \beta_{end}]$, which depends on P.

For each data sample (view, ch, seg), and corresponding ray $(\beta, \gamma, v)$ the following steps are performed:

locate a corresponding image pixel x, which is found by an intersection of the reconstruction plane P and ray $(\beta, \gamma, v)$, find all measured complementary rays $(\beta_n, \gamma_n, v_n)$, where n=N . . . −N, through x and N is the number of helical half turns. The complementary coordinates are given by:

$$\beta_n(\beta, \gamma) = \begin{cases} \beta + 2\gamma + n\pi, & n \text{ odd} \\ \beta + 2n\pi, & n \text{ even}, \end{cases}$$

$$\gamma_n(\gamma) = \begin{cases} -\gamma, & n \text{ odd} \\ \gamma, & n \text{ even}, \end{cases}$$

$$v_n(\beta, \gamma, v) = \begin{cases} \Delta z_n R / L^C, & n \text{ odd} \\ \Delta z_n R / L, & n \text{ even} \end{cases}$$

where $\Delta z_n = \Delta \beta_n H/2$; and $\rho \beta_n = \beta_S - \beta_n$, where $\beta_S$ is the view angle corresponding to the image slice position ($z_0 = \beta_S H/2$;), H is the helical pitch, $L = \Delta z R/v$ and $L^c = 2 R \cos \gamma - L$, and weight the data $g(\beta, \gamma, v)$ depending on the ray position, and normalize by the weighted contributions of all complementary rays.

The cone beam weighting function is given by:

$$w_{CB}(\beta, \gamma, v) = \frac{u_{FB}(\beta) \cdot u_{CB}(v, \gamma)}{\sum_{n=-N}^{N} (u_{FB}(\beta_n(\beta, \gamma)) \cdot u_{CB}(v_n))}$$

Note that in the summation the index n=0 corresponds to the direct ray: $\beta_0 = \beta$, and $v_0 = v$.

Figure 3:
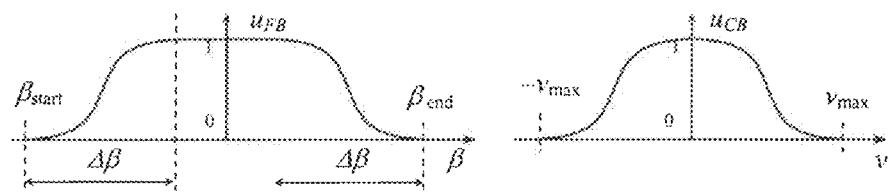
FIG. 3 illustrates the fan-beam and cone-beam weighting functions.

Examples of functions $u_{FB}(\beta)$ (fan beam) and $u_{CB}(v, \gamma)$ (cone beam) are shown in FIG. 3. The functions $u_{FB}(\beta)$ and $u_{CB}(v, \gamma)$ are called auxiliary weighting functions. Here $\Delta\beta$ is called the smoothing interval. It can be given as a fixed number of views, as a fixed angular range (for example 10°), or as a percentage of the angular scan length ($\beta_{end} - \beta_{start}$). It can be as small as 0% or as large as 50%.

The function $u_{FB}(\beta)$ is given by:

$$u_{FB}(\beta) = \begin{cases} 0, & \beta < \beta_{start} \\ p\left(\frac{\beta - \beta_{start}}{\Delta\beta}\right), & \beta_{start} \leq \beta < \beta_{start} + \Delta\beta \\ 1, & \beta_{start} + \Delta\beta \leq \beta \leq \beta_{end} - \Delta\beta \\ p\left(\frac{\beta_{end} - \beta}{\Delta\beta}\right), & \beta_{end} - \Delta\beta < \beta \leq \beta_{end} \\ 0, & \beta > \beta_{end} \end{cases}$$

Here the function p( ) can be chosen in various ways. Some examples:

Linear: $p(x) = x$.

Polynominal: $p(x) = 3x^2 - 2x^3$.

Trigonometric: $p(x) = \frac{1}{2}(1 - \cos(\pi x))$ or $p(x) = \sin^2\left(\frac{\pi x}{2}\right)$ In general, function p( ) is any function that satisfies: p(0)=0, p(1)=1, and p monotonically increases from 0 to 1.

The function $u_{CB}(v, \gamma)$ can be implemented in various ways. For example it can be given by:

$$u_{CB}(v) = \begin{cases} 0, & v < -v_{max} \\ p\left(\frac{v + v_{max}}{\Delta v}\right), & -v_{max} \leq v < -v_{max} + \Delta v \\ 1, & -v_{max} + \Delta v \leq v \leq v_{max} - \Delta v \\ p\left(\frac{v_{max} - v}{\Delta v}\right) & v_{max} - \Delta v < v \leq v_{max} \\ 0, & v > v_{max} \end{cases}$$

Here $\Delta v$ is called the smoothing interval. It can be given as a fixed length (for example 3.2 mm, or 3.2 segments), or as a percentage of the detector height $2v_{max}$. It can be as small as 0% or as large as 50%. The function p( ) can be chosen as discussed above.

Another version, $u_{CB}(v, \gamma)$ can be given by:

$$u_{CB}(v, \gamma) = \begin{cases} 0, & v < v_-(\gamma) - \delta v_-(\gamma) \\ p\left(\frac{v - v_-(\gamma) + \delta v_-(\gamma)}{2\delta v_-(\gamma)}\right), & v_-(\gamma) - \delta v_-(\gamma) \leq v < -v_-(\gamma) + \delta v_-(\gamma) \\ 1, & v_-(\gamma) + \delta v_-(\gamma) \leq v \leq v_+(\gamma) - \delta v_+(\gamma) \\ p\left(\frac{v_+(\gamma) + \delta v_+(\gamma) - v}{2\delta v_+(\gamma)}\right), & v_+(\gamma) - \delta v_+(\gamma) < v \leq v_+(\gamma) + \delta v_+(\gamma) \\ 0, & v > v_+(\gamma) + \delta v_+(\gamma) \end{cases}$$

where $v_+(\gamma)$ and $v_-(\gamma)$ are the boundaries of the n-PI window and are given by:

$$v_+(\gamma, n) = \frac{H(2\gamma + n\pi)}{4\pi\cos\gamma}$$

$$v_-(\gamma, n) = \frac{H(2\gamma - n\pi)}{4\pi\cos\gamma}$$

and n is equal to either 1 or 3, depending on the helical pitch. Here $\delta v_+(\gamma)$ and $\delta v_-(\gamma)$ are called the smoothing intervals. They can be given as a fixed length (for example 3.2 mm, or 3.2 segments), or as a percentage of the detector height $2v_{max}$. It can be as small as 0% or as large as 50%. It can also be proportional to:

$$\delta v_+(\gamma) = C(v_{max} - v_+(\gamma))$$

$$\delta v_-(\gamma) = C(v_{max} + v_-(\gamma)),$$

where C is the proportionality constant, 0<=C<=1.

The function p( ) can be chosen as discussed above, except for it should satisfy an additional condition: p(0.5)=0.5.

Figure 4:
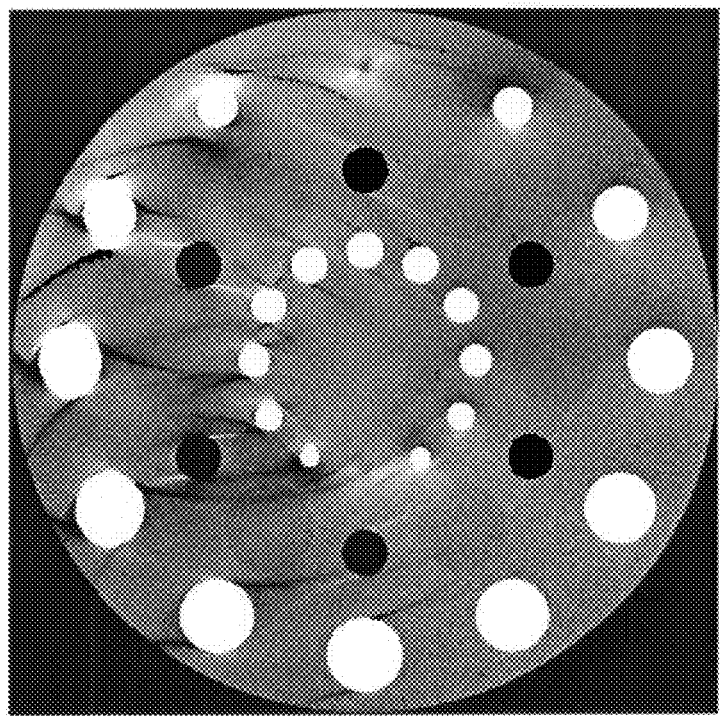
FIG. 4 is a conventional image of a disk phantom.
Figure 5:
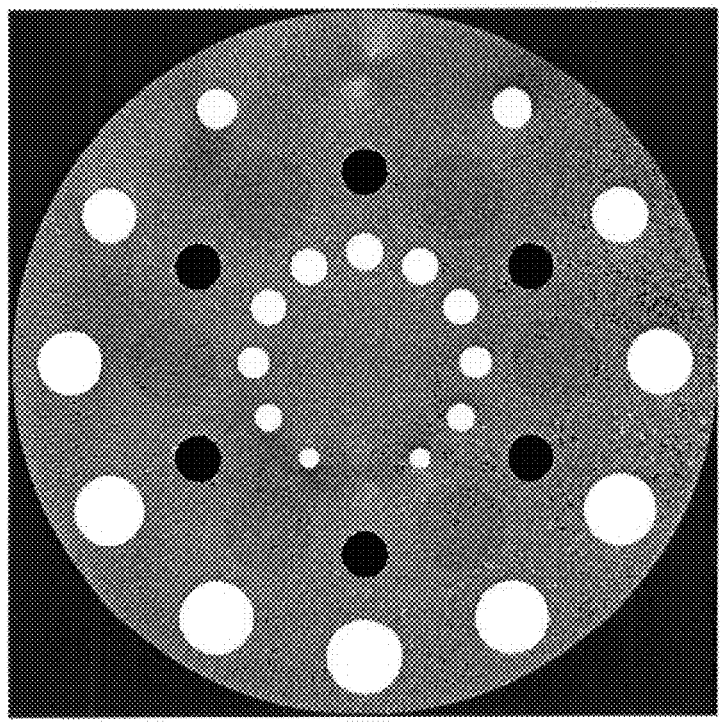
FIG. 5 is an image of the disk phantom according to the invention.

Images prepared according to the invention are shown in FIGS. 4-7. FIG. 4 shows a conventional image of a disk phantom obtained using a 320 by 0.5 detector and a helical pitch of 136 mm/rev. The image shown in FIG. 5 was obtained under the same conditions but was processed according to the invention. FIG. 5 is of much better quality.

Figure 6:
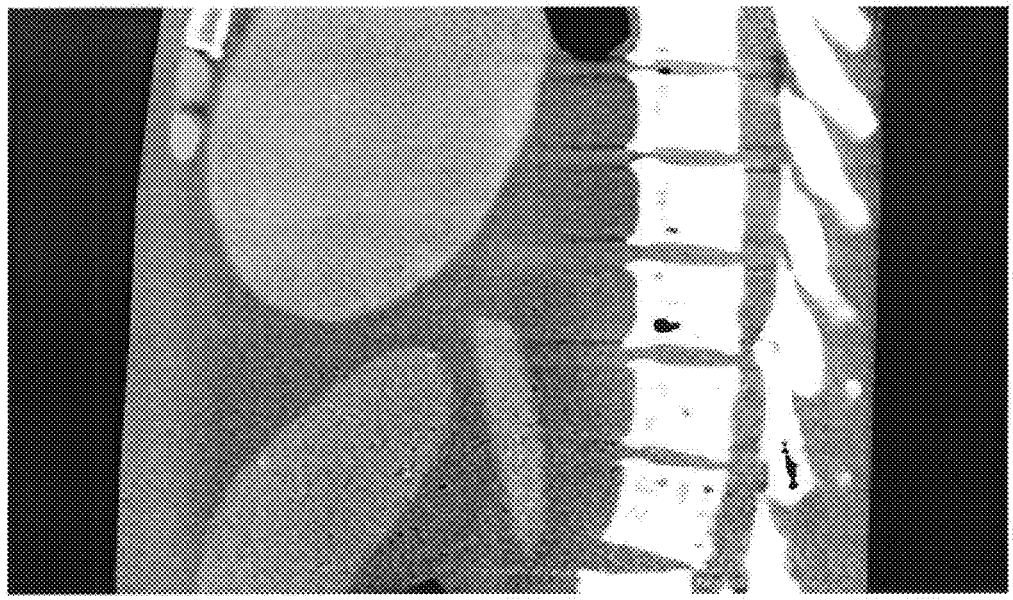
FIG. 6 is a conventional image of a chest phantom.
Figure 7:
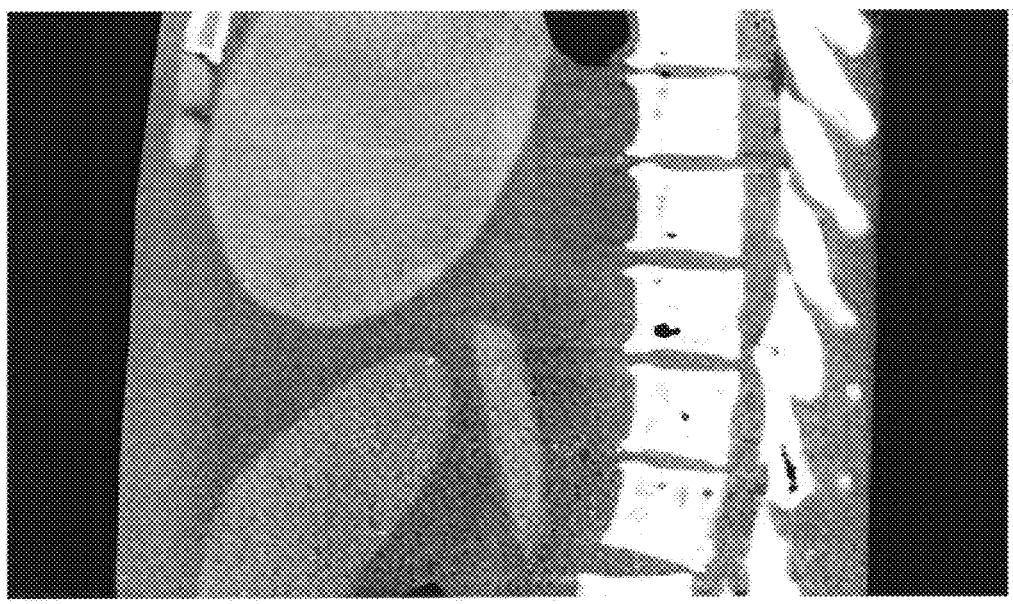
FIG. 7 is an image of the chest phantom according to the invention.
Figure 8:
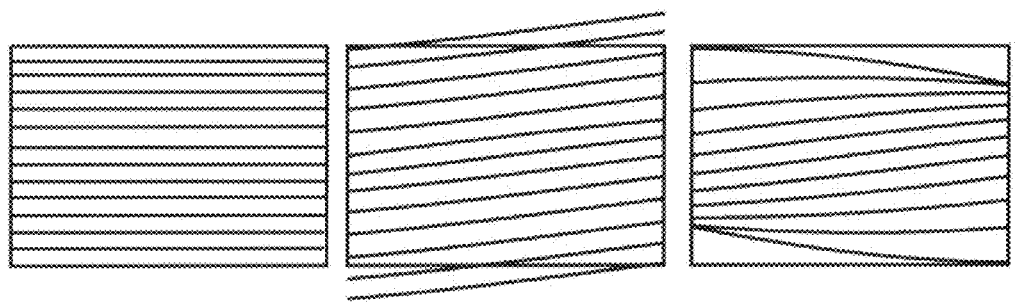
FIG. 8 is a diagram of conventional filtering and filtering according to the invention.

Similarly, FIG. 6 is a conventional image of a chest phantom while FIG. 7 is an image obtained using the present invention. Again, FIG. 7 is of much better quality where the appearance of many artifacts is reduced One possible modification of the proposed method is when filtering is applied along non-horizontal filtering directions, as shown in FIG. 8.

The present invention may be implemented in software or in hardware. In particular the operation of the processing unit described above can be carried out as a software program run on a microprocessor or a computer. The software can be stored on a computer-readable medium and loaded into the system.

Numerous other modifications and variations of the present invention are possible in light of the above teachings. It is therefore to be understood that within the scope of the appended claims, the invention may be practiced otherwise than as specifically described herein.

The invention claimed is:
1. A computed-tomography apparatus, comprising:
an x-ray source;
an x-ray detector disposed to receive x-rays from said x-ray source;
a data collection unit;

a processing unit for processing said data using a weighting function given as $$w_{CB}(\beta, \gamma, v) = \frac{u_{FB}(\beta) \cdot u_{CB}(v, \gamma)}{\sum_{n=-N}^{N} (u_{FB}(\beta_n(\beta, \gamma)) \cdot u_{CB}(v_n))}$$

where $\beta$ is a projection angle of said x-rays, $\gamma$ is a fan angle of said x-rays, N is a number of helical half-turns, n is an index of complementary rays and $v$ is a detector coordinate parallel to axis of rotation of said x-ray source, and wherein said processing uses said weighting function where:

$$u_{CB}(v, \gamma) = \begin{cases} 0, & v < v_-(\gamma) - \delta v_-(\gamma) \\ p\left(\frac{v - v_-(\gamma) + \delta v_-(\gamma)}{2\delta v_-(\gamma)}\right), & v_-(\gamma) - \delta v_-(\gamma) \le v < -v_-(\gamma) + \delta v_-(\gamma) \\ 1, & v_-(\gamma) + \delta v_-(\gamma) \le v \le v_+(\gamma) - \delta v_+(\gamma) \\ p\left(\frac{v_+(\gamma) + \delta v_+(\gamma) - v}{2\delta v_+(\gamma)}\right), & v_+(\gamma) - \delta v_+(\gamma) < v \le v_+(\gamma) + \delta v_+(\gamma) \\ 0, & v > v_+(\gamma) + \delta v_+(\gamma) \end{cases}$$

where $v_+(\gamma)$ and $v_-(\gamma)$ are boundaries of an n-PI window and $\delta v_+(\gamma)$ and $\delta v_-(\gamma)$ are smoothing intervals.

2. An apparatus as recited in claim 1, wherein said processing uses said weighting function where:

$$u_{FB}(\beta) = \begin{cases} 0, & \beta < \beta_{start} \\ p\left(\frac{\beta - \beta_{start}}{\Delta\beta}\right), & \beta_{start} \le \beta < \beta_{start} + \Delta\beta \\ 1, & \beta_{start} + \Delta\beta \le \beta \le \beta_{end} - \Delta\beta \\ p\left(\frac{\beta_{end} - \beta}{\Delta\beta}\right), & \beta_{end} - \Delta\beta < \beta \le \beta_{end} \\ 0, & \beta > \beta_{end} \end{cases}$$

where $\beta_{start}$ and $\beta_{end}$ are the start and end angles of a scan, respectively, p( ) is any function that satisfies: p(0)=0, p(1)=1, and p monotonically increases from 0 to 1.

3. An apparatus as recited in claim 1, wherein said processing unit comprises a filtering sub-unit that applies filtering along detector rows.

4. An apparatus as recited in claim 1, wherein said processing unit comprises a filtering sub-unit that applies filtering in directions other than along detector rows.

5. An apparatus as recited in claim 1, wherein said processing uses said weighting function where:

$$\beta v_+(\gamma) = C(v_{max} - v_+(\gamma))$$

$$\beta v_-(\gamma) = C(v_{max} + v_-(\gamma))$$

$$v_+(\gamma, n) = H(2\gamma + n\pi)/4\pi\cos\gamma$$

$$v_-(\gamma, n) = H(2\gamma - n\pi)/4\pi\cos\gamma$$

C is a proportionality constant, 0<C<1, n equals 1 or 3, and H is a helical pitch.

6. A computed tomography method, comprising:
exposing a subject to x-rays from an x-ray source;
collecting data;
processing said data comprising weighting said data using a weighting function given as $$w_{CB}(\beta, \gamma, v) = \frac{u_{FB}(\beta) \cdot u_{CB}(v, \gamma)}{\sum_{n=-N}^{N} (u_{FB}(\beta_n(\beta, \gamma)) \cdot u_{CB}(v_n))}$$

where $\beta$ is a projection angle of said x-rays, $\gamma$ is a fan angle of said x-rays, N is a number of helical half turns, n is an index of complementary rays and $v$ is a detector coordinate parallel to axis of rotation of said x-ray source; and
reconstructing an image of said subject using said weighted data,
wherein said processing comprises using said weighting function where:

$$u_{CB}(v, \gamma) = \begin{cases} 0, & v < v_-(\gamma) - \delta v_-(\gamma) \\ p\left(\frac{v - v_-(\gamma) + \delta v_-(\gamma)}{2\delta v_-(\gamma)}\right), & v_-(\gamma) - \delta v_-(\gamma) \le v < -v_-(\gamma) + \delta v_-(\gamma) \\ 1, & v_-(\gamma) + \delta v_-(\gamma) \le v \le v_+(\gamma) - \delta v_+(\gamma) \\ p\left(\frac{v_+(\gamma) + \delta v_+(\gamma) - v}{2\delta v_+(\gamma)}\right), & v_+(\gamma) - \delta v_+(\gamma) < v \le v_+(\gamma) + \delta v_+(\gamma) \\ 0, & v > v_+(\gamma) + \delta v_+(\gamma) \end{cases}$$

where $v_+(\gamma)$ and $v_-(\gamma)$ are boundaries of an n-PI window, $\delta v_+(\gamma)$ and $\delta v_-(\gamma)$ are smoothing intervals and p( ) is any function that satisfies: p(0)=0, p(0.5)=0.5, p(1)=1, and p monotonically increases from 0 to 1.

7. A method as recited in claim 6, wherein said processing comprises using said weighting function where:

$$u_{FB}(\beta) = \begin{cases} 0, & \beta < \beta_{start} \\ p\left(\frac{\beta - \beta_{start}}{\Delta\beta}\right), & \beta_{start} \le \beta < \beta_{start} + \Delta\beta \\ 1, & \beta_{start} + \Delta\beta \le \beta \le \beta_{end} - \Delta\beta \\ p\left(\frac{\beta_{end} - \beta}{\Delta\beta}\right), & \beta_{end} - \Delta\beta < \beta \le \beta_{end} \\ 0, & \beta > \beta_{end} \end{cases}$$

where p( ) is any function that satisfies: p(0)=0, p(1)=1, $\beta_{start}$ and $\beta_{end}$ are the start and end angles of a scan, respectively, and p monotonically increases from 0 to 1.

8. A method as recited in claim 6, wherein said processing comprises filtering along detector rows.

9. A method as recited in claim 6, wherein said processing comprises filtering in directions other than along detector rows.

10. A method as recited in claim 6, wherein said processing comprises using said weighting function where:

$$\beta v_+(\gamma) = C(v_{max} - v_+(\gamma))$$

$$\beta v_-(\gamma) = C(v_{max} + v_-(\gamma))$$

$$v_+(\gamma, n) = H(2\gamma + n\pi)/4\pi\cos\gamma$$

$$v_-(\gamma, n) = H(2\gamma - n\pi)/4\pi\cos\gamma$$

C is a proportionality constant, 0<C<1, n equals 1 or 3, and H is a helical pitch.

11. A non-transitory computer-readable medium containing instructions that may be executed by a computer to perform a method comprising:
- collecting data associated with exposing a subject to x-rays from an x-ray source;
- weighting said data using a weighting function given as $$w_{CB}(\beta, \gamma, v) = \frac{u_{FB}(\beta) \cdot u_{CB}(v, \gamma)}{\sum_{n=-N}^{N}(u_{FB}(\beta_n(\beta, \gamma)) \cdot u_{CB}(v_n))}$$

where $\beta$ is a projection angle of said x-rays, $\gamma$ is a fan angle of said x-rays, N is a number of helical half turns, n is an index of complementary rays and $v$ is a detector coordinate parallel to axis of rotation of said x-ray source; and
reconstructing an image of said subject using said weighted data, where:

$$u_{CB}(v, \gamma) = \begin{cases} 0, & v < v_-(\gamma) - \delta v_-(\gamma) \\ p\left(\frac{v - v_-(\gamma) + \delta v_-(\gamma)}{2\delta v_-(\gamma)}\right), & v_-(\gamma) - \delta v_-(\gamma) \leq v < -v_-(\gamma) + \delta v_-(\gamma) \\ 1, & v_-(\gamma) + \delta v_-(\gamma) \leq v \leq v_+(\gamma) - \delta v_+(\gamma) \\ p\left(\frac{v_+(\gamma) + \delta v_+(\gamma) - v}{2\delta v_+(\gamma)}\right), & v_+(\gamma) - \delta v_+(\gamma) < v \leq v_+(\gamma) + \delta v_+(\gamma) \\ 0, & v > v_+(\gamma) + \delta v_+(\gamma) \end{cases}$$

and where $v_+(\gamma)$ and $v_-(\gamma)$ are boundaries of an n-PI window, $\beta v_+(\gamma)$ and $\beta v_-(\gamma)$ are smoothing intervals and p( ) is any function that satisfies: p(0)=0, p(0.5)=0.5, p(1)=1, and p monotonically increases from 0 to 1.

12. A medium as recited in claim 11, wherein said method comprises using said weighting function where:

$$u_{FB}(\beta) = \begin{cases} 0, & \beta < \beta_{start} \\ p\left(\frac{\beta - \beta_{start}}{\Delta\beta}\right), & \beta_{start} \leq \beta < \beta_{start} + \Delta\beta \\ 1, & \beta_{start} + \Delta\beta \leq \beta \leq \beta_{end} - \Delta\beta \\ p\left(\frac{\beta_{end} - \beta}{\Delta\beta}\right), & \beta_{end} - \Delta\beta < \beta \leq \beta_{end} \\ 0, & \beta > \beta_{end} \end{cases}$$

where p( ) is any function that satisfies: p(0)=0, p(1)=1, $\beta_{start}$ and $\beta_{end}$ are the start and end angles of a scan, respectively, and p monotonically increases from 0 to 1.

13. A medium as recited in claim 11, wherein said method comprises filtering along detector rows.

14. A medium as recited in claim 11, wherein said method comprises filtering in directions other than along detector rows.

15. A medium as recited in claim 11, wherein said method comprises using said weighting function where:

$\beta v_+(\gamma) = C(v_{max} - v_+(\gamma))$ $\beta v_-(\gamma) = C(v_{max} + v_-(\gamma))$ $v_+(\gamma, n) = H(2\gamma + n\pi)/4\pi\cos\gamma$ $v_-(\gamma, n) = H(2\gamma - n\pi)/4\pi\cos\gamma$ C is a proportionality constant, 0<C<1, n equals 1 or 3, and H is a helical pitch.

* * * * *